United States Patent [19]

Fischer

[11] Patent Number: Plant 6,638

[45] Date of Patent: Feb. 28, 1989

[54] AFRICAN VIOLET PLANT NAMED IRISH RUFFLES

[76] Inventor: Arnold Fischer, Kahlendamm 22, 3000 Hannover 51, Fed. Rep. of Germany

[21] Appl. No.: 85,089

[22] Filed: Aug. 13, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A cultivar of African violet plant named Irish Ruffles, characterized by its white flower color with ruffled light green edges, large single flowers, medium green foliage, compact growth habit, and its floriferous habit.

1 Drawing Sheet

The present invention comprises a new and distinct cultivar of African violet plant, botanically known as *Saintpaulia ionantha,* named Irish Ruffles.

The new cultivar is a product of a planned breeding program carried out by applicant in Hannover, Federal Republic of Germany. The basic objective of the breeding program was to create a new African violet cultivar having single green and white bicolored flowers with ruffled edges, ruffled foliage, a highly floriferous habit, and a compact growth habit. The new cultivar was originated from a cross made by applicant in the controlled breeding program. Both the female (or seed) and the male (or pollen) parents are unnamed and not identifiable at this time.

Irish Ruffles was discovered and selected by applicant as a flowering plant with the progeny of the stated cross in a controlled environment in Hannover, Federal Republic of Germany. Asexual reproduction of the new cultivar by leaf cuttings, as performed by applicant at Hannover, Federal Republic of Germany, has demonstrated that the combination of characteristics as herein disclosed for the new cultivar are firmly fixed and retained through successive generations of asexual reproduction.

Irish Ruffles has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Irish Ruffles which in combination distinguish this african violet as a new and distinct cultivar:

(1) Large single zygomorphic rotate flowers with an extremely ruffled margin, and 35–40 mm in diameter.

(2) Flowers are bi-colored with a white background and sections of green on the edges.

(3) Medium green pubescent foliage, oval shaped with slightly ruffled sinuate margins, cordate base and broadly acute apex.

(4) Compact rosette habit with flowers held erect on strong upright peduncles.

(5) Very floriferous, with flowers continuing to open for many weeks after the onset of flowering.

(6) Suitable for production in 10 cm pots, finishing in 9–13 weeks when started from a $2\frac{1}{4}''$ plantlet.

The new cultivar is similar in certain characteristics to Fairy Queen, disclosed in U.S. Plant Pat. No. 4,935. Irish Ruffles is principally distinguished from Fairy Queen by its less ruffled leaves, and green instead of rose colored picotee.

The accompanying photographic drawing shows a typical specimen plant of the new cultivar. The photograph is in black and white, with certain leaves and flowers being colored to show the green petal edges. The colors depict true color as stated in the color values below.

In the following description, color references are made to The Royal Horticultural Society Colour Chart (R.H.S.), except where general colors or ordinary significance are referred to. Color values were taken under fluorescent light conditions at approximately 4:00 p.m. in Parrish, Fla.

Botanical classification: *Saintpaulia ionantha,* Ramat., cv. Irish Ruffles.

Parentage: Unknown.

Propagation: The new cultivar holds its distinguishing characteristics through successive propagations by leaf cuttings.

Plant: From 4 cm to 10 cm tall when grown in pots, and approximately 22 cm in diameter when fully grown. The growth rate is vigorous, and the general shape of the fully grown plant is round.

*Leaves.*—Quantity: Abundant. Shape: Oval with ruffled sinuate margins. Diameter: Up to 8 cm for a mature leaf. Texture: Pubescent, glossy. Ribs and veins: Pinnate. Color (upper side): 137 A. Color (under side): 138 D. Petioles: Light green.

*Flowers.*—Buds: Size: About 1 cm×1 cm. Shape: Round. Rate of opening: Normal. Sepals: Shape: Lanceolate. Color: Light green. Phyllaries: 2, lanceolate. Color: 137 B. Calyx: Shape: Funnel. Size: 12–14 mm in diameter. Aspect: Pubescent. Peduncle: Length: Up to 9 cm. Character: Erect, rigid. Color: Light green.

*Individual flowers.*—Number of petals: 5. Size: 35–40 mm in diameter and 10–15 mm deep Shape: Cup shaped when bloom first opens, becoming flat as bloom matures. Color (upper side): Clear white with sections of 144D along the edges. Color (under side): Same as upper side Flowers fade slightly as they age. The flower color may vary somewhat depending upon the amount of light, fertilizer, temperature and other growing conditions. Borne: Cymose clusters on upright peduncles, up to 9 cm long. Flowering habit: Flowers profusely and intermittently year round, with blooms lasting 2–3 weeks after which petals dry up but do not drop. Finishes in 9–12 weeks when a 2¼" plantlet is placed in a 10 cm pot.

*Reproductive organs.*—Stamens: Stamens borne singly on one side of ovary; 2 anthers basifixed. Anthers: 2 mm×2 mm, yellow. Filaments: 3 mm, white. Pollen Color: Pale yellow. Pistils: Number: 1. Styles: 1, 6–7 mm in length. Stigma: Sticky, white. Ovaries: Superior.

*Roots.*—Fibrous and fine.

Disease resistance: No african violet diseases observed to date.

I claim:

1. A new and distinct cultivar of African violet plant named Irish Ruffles, as illustrated and described, and particularly characterized by its white flower color with ruffled light green edges, large single flowers, medium green foliage, compact growth habit, and its floriferous habit.

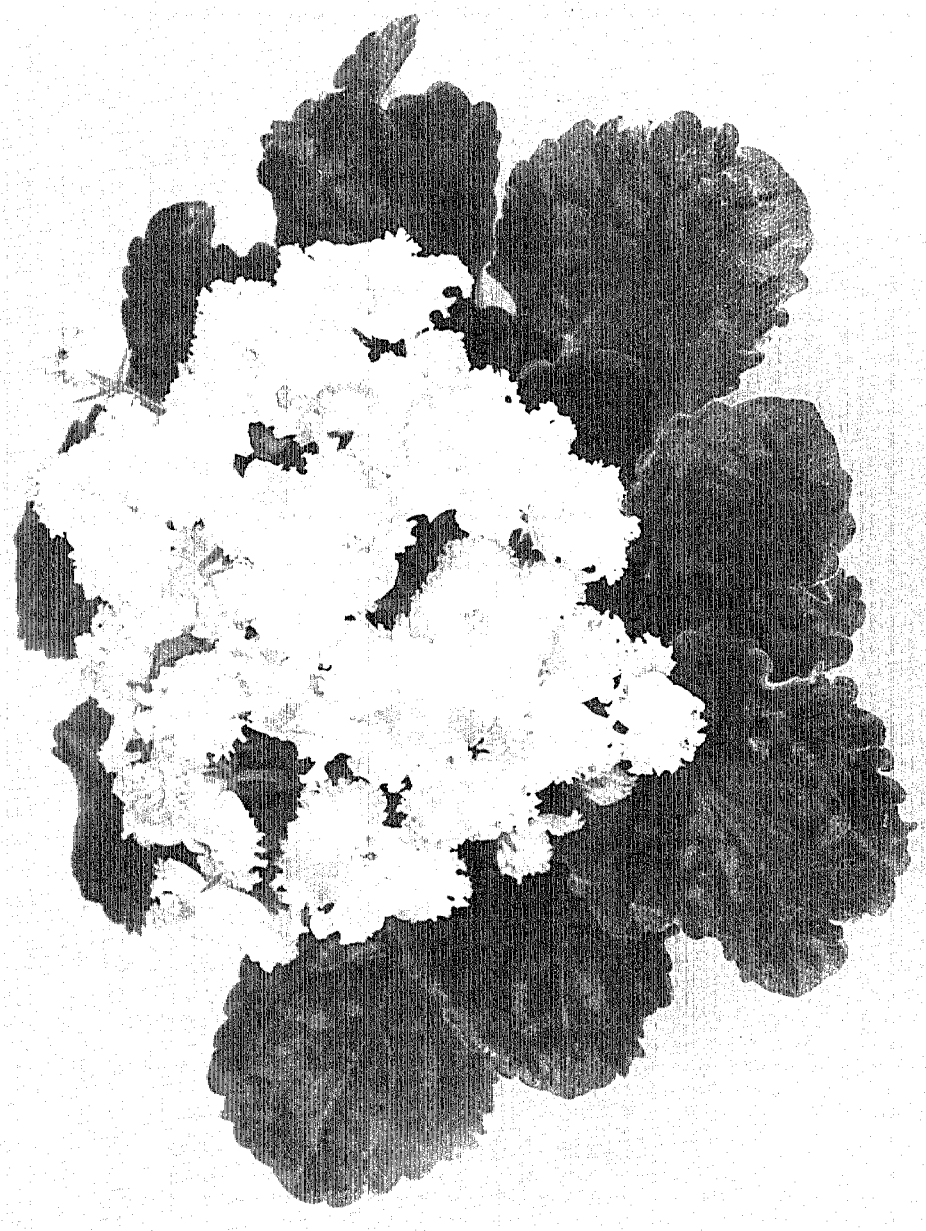

* * * * *